(12) United States Patent
Mordaunt et al.

(10) Patent No.: US 10,912,677 B2
(45) Date of Patent: *Feb. 9, 2021

(54) MULTI-SPOT OPTICAL FIBER ENDOPHOTOCOAGULATION PROBE

(71) Applicant: TOPCON MEDICAL LASER SYSTEMS INC., Santa Clara, CA (US)

(72) Inventors: David H. Mordaunt, Los Gatos, CA (US); Dan E. Andersen, Menlo Park, CA (US)

(73) Assignee: TOPCON MEDICAL LASER SYSTEMS INC., Santa Clara, CA (US)

( * ) Notice: Subject to any disclaimer, the term of this patent is extended or adjusted under 35 U.S.C. 154(b) by 100 days.

This patent is subject to a terminal disclaimer.

(21) Appl. No.: 16/159,266

(22) Filed: Oct. 12, 2018

(65) Prior Publication Data

US 2019/0046352 A1 Feb. 14, 2019

Related U.S. Application Data

(63) Continuation of application No. 11/726,991, filed on Mar. 22, 2007, now Pat. No. 10,098,781.

(60) Provisional application No. 60/785,552, filed on Mar. 24, 2006.

(51) Int. Cl.
*A61F 9/008* (2006.01)
*A61B 18/00* (2006.01)
*A61B 18/22* (2006.01)

(52) U.S. Cl.
CPC .......... *A61F 9/008* (2013.01); *A61F 9/00821* (2013.01); *A61B 2018/00636* (2013.01); *A61B 2018/2211* (2013.01); *A61F 2009/00863* (2013.01); *A61F 2009/00897* (2013.01)

(58) Field of Classification Search
CPC ................ A61F 9/008; A61F 9/00821; A61F 2009/00863; A61F 2009/00897; A61B 2018/00636; A61B 2018/2211
USPC .................................................. 606/4–6, 15
See application file for complete search history.

(56) References Cited

U.S. PATENT DOCUMENTS

| | | |
|---|---|---|
| 4,884,884 A | 12/1989 | Reis |
| 4,917,486 A | 4/1990 | Raven et al. |
| 5,192,278 A | 3/1993 | Hayes et al. |
| 5,261,904 A | 11/1993 | Baker et al. |
| 5,336,216 A | 8/1994 | Dewey |
| 5,688,264 A | 11/1997 | Ren et al. |
| 5,779,696 A | 7/1998 | Berry et al. |

(Continued)

OTHER PUBLICATIONS

Final Office Action received for U.S. Appl. No. 11/726,991, dated Jan. 26, 2012, 18 pages.

(Continued)

*Primary Examiner* — Nathan J Jenness
(74) *Attorney, Agent, or Firm* — Dentons US LLP (57) ABSTRACT

A system and method for treating target tissue including a light source for generating a beam of light, a plurality of optical fibers, a deflection device configured to selectively deflect the light beam into the input ends of the optical fibers, one optical fiber input end at a time, and a probe having a tip with the output ends of the optical fibers and configured for insertion into target tissue. The probe tip is configured to sequentially project spaced apart spots of the light beam from the output ends as the deflection device deflects the light beam into the optical fibers. One or more moving or static deflecting optics at the probe tip can be used to statically or dynamically deflect the beam exiting the optical fibers.

40 Claims, 9 Drawing Sheets

(56) References Cited

U.S. PATENT DOCUMENTS

| | | |
|---|---|---|
| 5,921,981 A | 7/1999 | Bahmanyar et al. |
| 6,004,313 A | 12/1999 | Shimmick et al. |
| 6,020,988 A | 2/2000 | Deliwala et al. |
| 6,066,128 A | 5/2000 | Bahnnanyar et al. |
| 6,096,028 A | 8/2000 | Bahnnanyar et al. |
| 6,099,522 A | 8/2000 | Knopp et al. |
| 6,456,769 B1 | 9/2002 | Furusawa et al. |
| 7,146,983 B1 | 12/2006 | Hohla et al. |
| 2001/0055462 A1 | 12/2001 | Seibel |
| 2002/0013572 A1 | 1/2002 | Berlin |
| 2002/0013577 A1 | 1/2002 | Frey et al. |
| 2002/0045811 A1 | 4/2002 | Kittrell et al. |
| 2003/0220633 A1 | 11/2003 | Angeley et al. |
| 2005/0024720 A1 | 2/2005 | Cartlidge et al. |
| 2005/0078910 A1 | 4/2005 | Hickingbotham |
| 2006/0100677 A1 | 5/2006 | Blumenkranz et al. |
| 2006/0195076 A1 | 8/2006 | Blumenkranz et al. |

OTHER PUBLICATIONS

Final Office Action received for U.S. Appl. No. 11/726,991 dated Oct. 9, 2013, 18 pages.

Final Office Action received for U.S. Appl. No. 11/726,991, dated Aug. 5, 2014, 18 pages.

Non Final Office Action received for U.S. Appl. No. 11/726,991, dated Mar. 20, 2013, 14 pages.

Non Final Office Action received for U.S. Appl. No. 11/726,991, dated Sep. 22, 2011, 22 pages.

Non-Final Office Action received for U.S. Appl. No. 11/726,991, dated Mar. 26, 2014, 15 pages.

International Preliminary Report on Patentability received for PCT Patent Application No. PCT/US2007/007307, dated Sep. 30, 2008, 7 pages.

International Search Report and Written Opinion received for PCT Patent Application No. PCT/US2007/007307, dated Mar. 4, 2008, 7 pages.

FIG. 17

MULTI-SPOT OPTICAL FIBER ENDOPHOTOCOAGULATION PROBE

This application is a continuation of U.S. application Ser. No. 11/726,991 filed Mar. 22, 2007 which claims the benefit of U.S. Provisional Application No. 60/785,552 filed Mar. 24, 2006.

FIELD OF THE INVENTION

The present invention relates to photothermal treatment of retinal tissue using fiber-optic-based endophotocoagulation probes.

BACKGROUND OF THE INVENTION

Laser photocoagulation procedures used to treat retinal tears, diabetic retinopathy, and other retinal disorders are well known and widely used. There are essentially three main delivery devices utilized for the delivery of laser energy: the slit lamp, the laser indirect ophthalmoscope and the laser endophotocoagulation probe. The present invention deals with the latter.

Traditional ophthalmic surgical laser systems include a laser source connected to a single core, optical fiber endophotocoagulation probe. The probe is inserted into the eye, allowing for the delivery of spots of laser energy to the target tissue, one spot at a time. Each laser pulse is activated by the depression of a footswitch, and the parameters of the delivered laser pulse are typically controlled by a system control panel. The patient must be kept sedated for the duration of the procedure. This single-shot "step and repeat" approach is time consuming and tedious for the physician. The lengthy duration of the anesthesia required by the procedure, and the number of shots delivered, can put the patient at risk.

Simultaneous delivery of multiple spots in endoprobe therapy is known. For example, U.S. Pat. Nos. 5,921,981, and 6,066,128 and 6,096,028 disclose a single laser source connecting to a single core optical fiber, where the laser energy from the single fiber is simultaneously separated into multiple fibers each with equal laser energy. The advantage of this approach over single fiber endophotocoagulation probe delivery is that the speed of the procedure will be increased as N-fibers in the bundle of fibers yield N spots simultaneously. However, there are potential problems with this approach. For example, a much higher power laser source is required in order to deliver the N spots simultaneously. This is significantly more expensive than traditional systems, and there are limits to the amount of power that can be coupled into a specific fiber diameter and numerical aperture. There are also safety issues. If for some reason the components that separate the energy fail or are partially damaged then non-uniform energy will be delivered through the multi-fiber bundle. In the worst case, all the energy could be transmitted down a single fiber, and could result in significant over-treatment at one target tissue location. The system is also inflexible, as the number of spots delivered is fixed and always equal to the number of fibers in the multi-fiber bundle that receive the divided laser energy.

Accordingly, there is a need for a safe, cost effective, flexible and time-efficient approach to retinal photocoagulation with an endophotocoagulation probe that is not provided by known methods or devices.

SUMMARY OF THE INVENTION

The present invention solves the aforementioned problems by providing a system and method for treating target tissue that sequentially generates multiple spaced apart beam spots from a single tissue probe from a single light source.

A photomedical system for treating target tissue includes a light source for generating a beam of light, a plurality of optical fibers each having an input end and an output end, a deflection device configured to selectively deflect the light beam into the input ends of the optical fibers, one optical fiber input end at a time, and a probe having a tip configured for insertion into target tissue, wherein the output ends of the optical fibers terminate at the probe tip; and wherein the probe tip is configured to sequentially project spaced apart spots of the light beam from the output ends as the deflection device deflects the light beam into the input ends of the optical fibers one optical fiber input end at a time.

In another aspect, a photomedical system for treating target tissue includes a light source for generating a beam of light, an optical fiber having an input end configured to receive the beam of light and an output end configured to project the beam of the light, a probe having a tip configured for insertion into target tissue, wherein the output end of the optical fiber terminates at the probe tip, at least one optical element disposed adjacent the output end for deflecting the projected beam of light, and a device for moving the at least one optical element to change a direction of the deflection of the projected beam of light.

A method for treating target tissue includes generating a beam of light, selectively deflecting the beam of light into input ends of a plurality of optical fibers, one optical fiber input end at a time, and projecting the beam of light out of output ends of the plurality of optical fibers, one optical fiber output end at a time, wherein the output ends of the optical fibers terminate at a tip of a probe configured for insertion into target tissue, and wherein the probe tip is configured to sequentially project spaced apart spots of the light beam from the output ends as the light beam is selectively deflected into the input ends of the optical fibers.

In another aspect, a method for treating target tissue includes generating a beam of light, focusing the beam of light into an input end of an optical fiber, projecting the beam of light out of an output end of the optical fiber, wherein the output end of the optical fiber terminates at a tip of a probe configured for insertion into target tissue, deflecting the projected beam of light using an optical element disposed adjacent the output end of the optical fiber, and moving the optical element to change a direction of the deflection of the projected beam of light.

Other objects and features of the present invention will become apparent by a review of the specification, claims and appended figures.

DETAILED DESCRIPTION OF THE PREFERRED EMBODIMENTS

Figure 1:
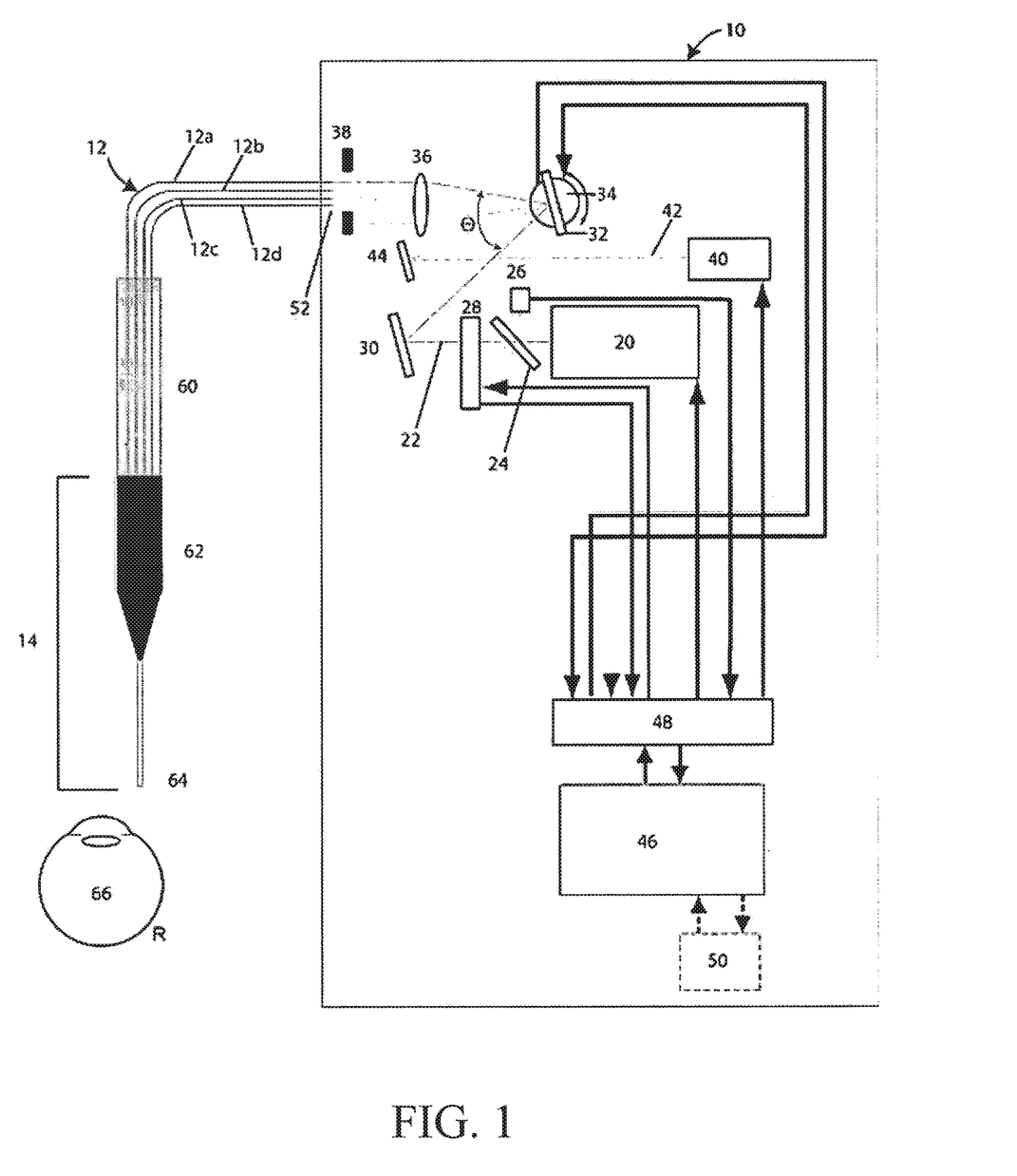
FIG. 1 is a schematic diagram of the light generating unit, fiber bundle, and endophotocoagulation probe, using a movable mirror to selectively deflect the beam into select fibers in the optical fiber bundle.

The invention is a system and technique for automatically and sequentially delivering multiple spots of laser energy through a multi-fiber endophotocoagulation probe. A moving mirror or fiber switch is used to sequentially deflect light into separate input ends of individual optical fibers, to ultimately provide a sequential pattern of spots at the target tissue by switching between the individual fibers. An exemplary photothermal treatment system is schematically shown in FIG. 1, and includes a light generating unit 10, an optical fiber bundle 12, and an endophotocoagulation probe 14.

Light generating unit 10 includes a light source 20 that generates a treatment beam of light 22. Light source 20 can be any conventional source of visible or invisible light, such as lasers, laser diodes, flash lamps, light emitting diodes, etc. Beam 22 first encounters a mirror 24, which serves to reflect a small amount of the beam 22 to a photodiode 26 for measuring the intensity of beam 22 (for safety purposes). The beam 22 then encounters a shutter 28, which selectively blocks the beam 22 (as well as possibly gating the beam 22 to reduce its power). Turning mirror 30 then directs the beam 22 to a switching mirror 32. Mirror 32 is mounted on a deflection device 34 (e.g. a motor, galvo, etc.), which rotates the mirror 32 to change the deflection angle θ it imparts on the beam 22. Mirror 32 directs the beam through a lens 36 and selectively into the optical fibers in the optical fiber bundle 12, one at a time. Mirror 32 may also be used as a shutter, by directing light into a beam dump 38 instead of optical fiber bundle 12. In case invisible light is used to form beam 22 or the power of beam 22 cannot easily be reduced, a second light source 40 can be used to generate an aiming beam 42 which can be directed by a mirror 44 to mirror 32 (and then into optical fiber bundle 12). Aiming beam 42 can be used by the physician to visualize where the treatment beam 22 will impinge the target tissue before actual treatment. The light sources 20/40, shutter 28 and deflection device 34 can be controlled by a controller 46 via an input/output device or bus 48. A graphic user interface 50 can be used to input commands and otherwise control the operation of controller 46.

Fiber bundle 12 includes a plurality of individual optical fibers. In the exemplary embodiment shown in FIG. 1, there are four optical fibers 12a, 12b, 12c and 12d, each having an input end 52 and an output end 54. The input ends 52 are positioned such that mirror 32 selectively directs beam 22 into one of optical fibers 12a, 12b, 12c, 12d at any given time. Preferably, the input ends 52 are arranged in a line, so that the deflection device 34 need only have a single axis of rotation. Preferably, mirror 32 is positioned one focal length away from lens 36 to provide a telecentric scan of beam 22, thus allowing for the injection of beam 22 into all the fibers 12a, 12b, 12c, 12d on parallel paths to preserve the launch numerical aperture (NA) across the bundle 12. If needed, aiming beam 42 can be injected into the optical fiber bundle 12 to visualize the location(s) at which beam 22 will impinge the target tissue. Visualization of the treatment beam 22 or aiming beam 42 is preferably accomplished using direct visualization under magnification, such as through a biomicroscope. Light source 40 can be visible to the eye, or invisible if an alternate visualization scheme such as infrared imaging is employed. Beam 22 may also be visible, but need not be. Beam 22 can be used for visible or invisible alignment by simply reducing its power and either directly viewing or viewing using a visualization device such as an infrared camera.

Figure 2:
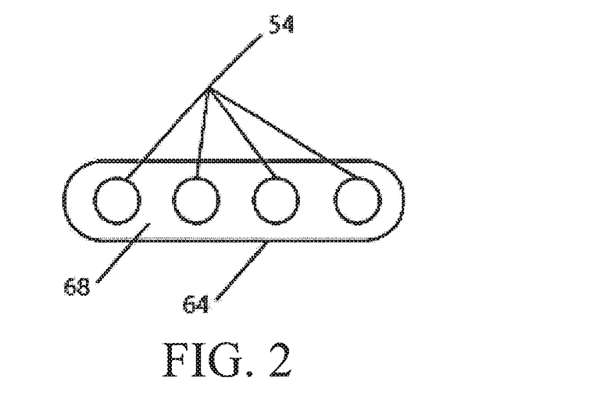
FIGS. 2-3 are end views of alternate configurations of the output ends of the optical fibers at the tip of the endophotocoagulation probe.
Figure 3:
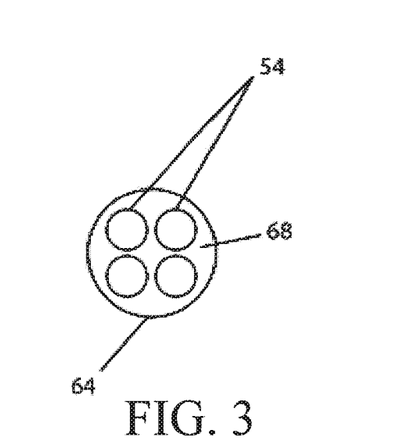

The probe 14 includes a jacket 60, a handle 62, and a tip 64. The fiber bundle 12 extends through the jacket 60 (for maintaining the fiber bundle), the handle 62 (which is gripped by the physician to manipulate the probe and the ultimate disposition of the beam 22 on the target tissue within the eye 66), and the tip 64 (which is inserted into the eye 66 and adjacent to the target tissue therein). The output ends 54 of optical fibers 12a, 12b, 12c, 12d are disposed in the tip 64 in a manner to produce the desired spot spacing at the target tissue. Ideally, the configuration of the output ends 54 in tip 64 nominally generates a plurality of laser spots of equal intensity, size, and separation. Common spot patterns are linear arrays (e.g. 2×1, 3×1, 4×1, etc.) and 2-dimensional arrays (e.g. 2×2, 3×2, 4×2, 3×3, 4×3, 4×4, etc.). FIGS. 2 and 3 illustrate the configuration of the output ends 54 in tip 64 for creating a linear 4×1 array or a two-dimensional 2×2 array of spot patterns, respectively, where tip 64 includes (or is formed by) a protective and sterilizable sheath 68 to secure the optical fiber output ends 54 in place. Tip 64 can be configured to be disposable in a cost effective manner.

Other pattern configurations are possible as well, such as circular or semicircular patterns that may be used to encircle retinal tears or lattice degenerations. The sequence of spots formed by light emitted from the output ends 54 can be staggered so that optical fibers with adjacent output ends do not emit sequentially. This can be accomplished by changing the relative positioning of the various fibers at the output ends 54 relative to the input ends 52, such that two fibers have input ends 52 that are adjacent to each other but their output end 54 are not adjacent to each. This allows mirror 32 to quickly switch the position of the beam 22 from fiber to adjacent fiber on the input ends 52 (i.e. to minimize the switching time), while providing treater spot separation between adjacent pulses of light using non-adjacent fiber output ends 54. Such a scheme aids in limiting the regional buildup of heat, and thus minimizing collateral tissue damage.

Figure 4:
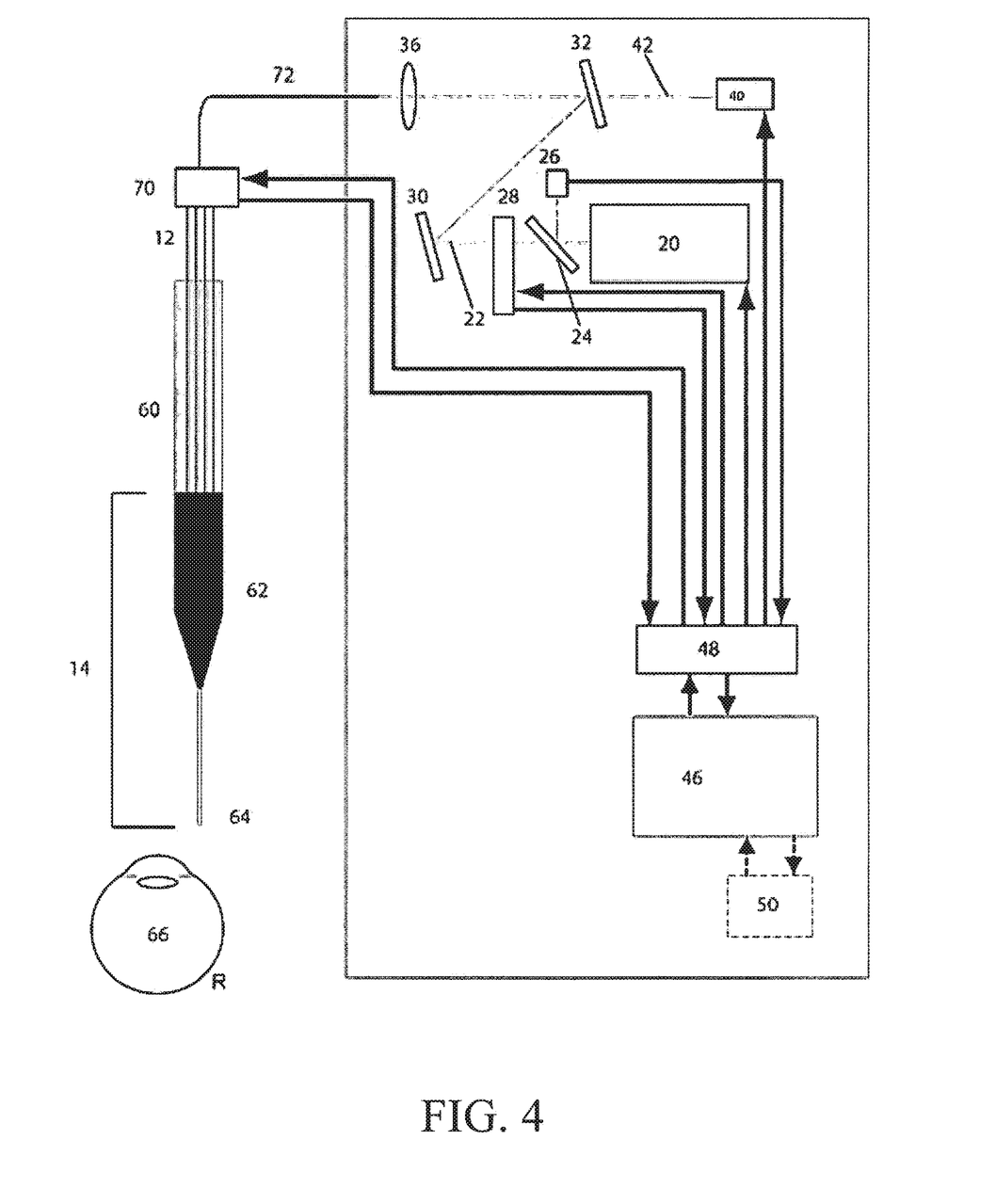
FIG. 4 is a schematic diagram of the light generating unit, fiber bundle, and endophotocoagulation probe, using a fiber optic switch to selectively inject the beam into the optical fiber bundle.

FIG. 4 illustrates an alternate configuration to that shown in FIG. 1, where mirror 32 is fixed, and instead a self contained, active fiber optic switch 70 is used that receives the beam 22 via an optical fiber 72, and sequentially directs the beam 22 into the optical fibers in bundle 12. Fiber switch 70 is preferably controlled by controller 46 via input/output device or bus 48. Fiber optic switches are well known in the art, and typically use electro-mechanical actuation systems to deflect the light beam into the various optical fibers in bundle 12. One example would be the Moog Fiber Optic Switch (pin: F04663R-A1FC-300), which has switching times of <15 ms when using 0.22 NA, 50 µm core fibers. In order to provide a disposable probe for sterility, fiber switch 70 is preferably made be made integral to the system, with multiple external fiber ports for attaching to each of the optical fibers in bundle 12. This way, the probe 14 along with the fiber bundle 12 may be discarded after a certain number of uses.

There are many advantages of using either the fiber switch 70 of FIG. 4 or the moving mirror 32 of FIG. 1, to the sequentially deflect beam 22 into the optical fibers of fiber bundle 12 (one at a time), because the order, number and location of the spots can by dynamically changed simply by dynamically changing which optical fibers (and their order) that will receive beam 22. The number of spots delivered may also be determined by the physician. Switching mirror 32 or fiber switch 70 can be configured to direct light to any number of fibers within the fiber bundle 12, including excluding some fibers and/or directing light to some fibers more often than others. This, allows the surgeon to adjust the numbers and locations of laser spots delivered depending on the clinical details of the procedure.

Figure 5:
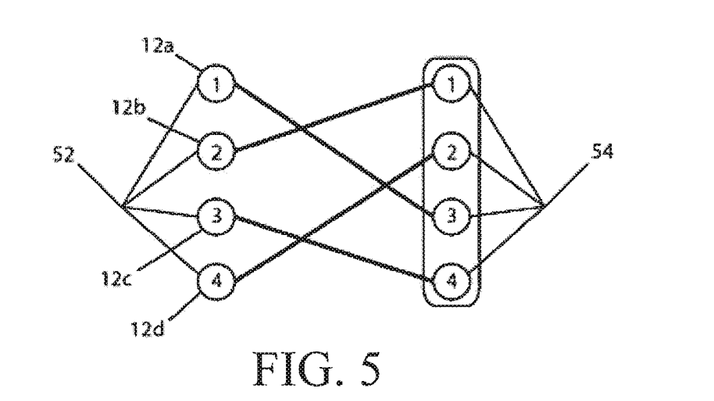
FIG. 5 is a diagram showing the configuration of the input and output ends of the optical fibers in the fiber bundle.

FIG. 5 illustrates how non-sequential spot emission can be achieved by not maintaining the fiber order between the input and output ends 52, 54 of the optical fibers in bundle 12. Specifically, in the case of input/output ends 52, 54 configured in 1×4 linear arrays, the input end 52 of fiber 12a is located at position 1 while its output end 54 is located at position 3. Likewise, the input ends 52 of fibers 12b, 12c and 12d are located at positions 2, 3 and 4, but their output ends 54 are located at positions 1, 4, and 2, respectively. This is but one example, where many other such schemes are possible. Because of symmetry, the schemes are different for even and odd numbers of fibers in the array.

Figure 6:
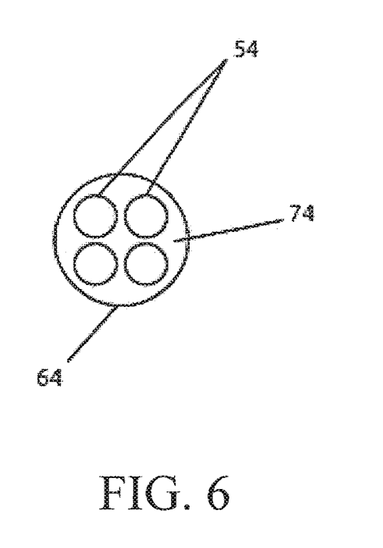
FIGS. 6-10 are end views of the output ends of the optical fibers at the tip of the endophotocoagulation probe, with alternate configurations of hollow and/or filled channels within the file bundle.
Figure 7:
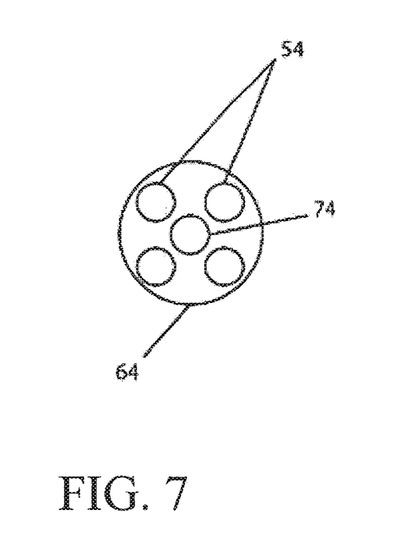
Figure 8:
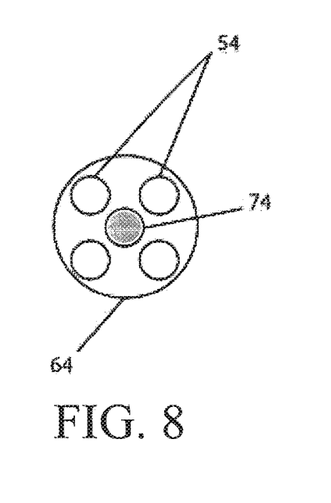
Figure 9:
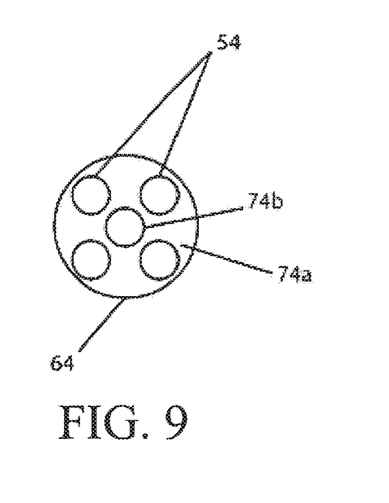
Figure 10:
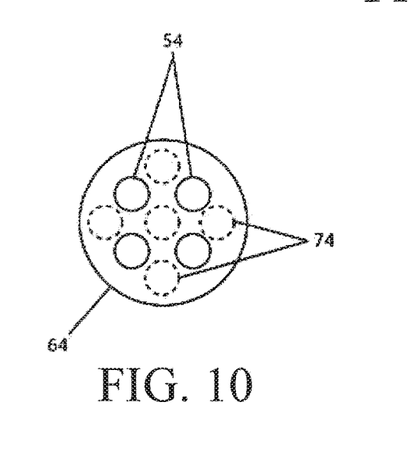

FIGS. 6-10 illustrate embodiments that include one or more channels 74 within fiber bundle 12 (and probe 14). Such channels may be hollow, or filled. A hollow channel may be used for irrigation and/or aspiration, such as is often needed in surgery. A filled channel may be used to convey illumination light to the target tissue and/or return imaging light to aid the surgeon's visualization of the target tissue. Specifically, FIG. 6 illustrates a channel 74 formed in the dead space surrounding the optical fibers and the outer wall of probe 64. FIG. 7 illustrates a hollow channel 74 formed as a separate hollow conduit extending down the center of the optical fibers. FIG. 8 illustrates a solid channel 74 (e.g. in the form of a solid conduit such as an optical fiber dedicated to visualization or illumination). FIG. 9 illustrates the combination of using the dead space between the fibers (e.g. see FIG. 6) as a first channel 74a and a separate conduit (hollow or filled) as the second channel 74b (e.g. see FIG. 7 or 8). FIG. 10 illustrates the combination of multiple fibers and multiple channels 74.

Figure 11:
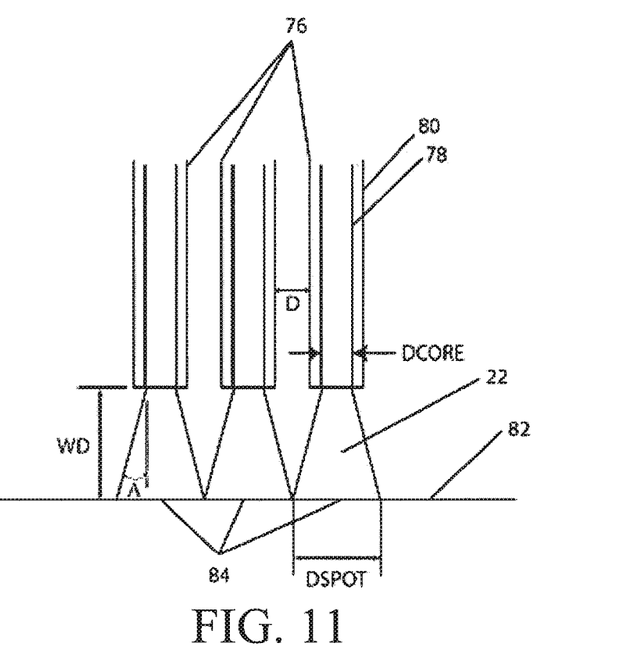
FIG. 11 is a side view illustrating the spots of light on the target tissue, and the working distance between the probe tip and the target tissue.

FIG. 11 schematically shows the geometry of a linear array of three optical fibers 76 at the end of probe tip 64. Each optical fiber 76 includes a light transmissive central core 78, and a cladding 80 surrounding the core 78. A jacket (not shown) may be present surrounding the cladding 80. The fibers 76 are separated by a distance D. The beam 22 exiting optical fibers 76 ultimately impinges on the target tissue 82 in spots 84 with a size (Dspot) given by the following relation (for small values of A):

$$D\text{spot} = (D\text{core} + 2*WD*A), \tag{1}$$

where Dcore is the diameter of the core 78, WD is the spacing (also called the working distance) between the end of the probe and the tissue, and A is angle of divergence of the beam 22 exiting the fiber. Rather than changing the energy of beam 22, a physician will often adjust the working distance WD in order to modify the clinical effect (i.e. by changing the intensity per unit area on the target tissue). However, in an array such as the one shown in FIG. 11, and using a conventionally sized fiber core diameter (e.g. 62.5 µm), the beam spots 84 can overlap at a working distance WD of around 1.5 mm (in water). This may not be ideal for those applications where there is a desired edge-to-edge separation between spots 84 of about one half a spot diameter (e.g. for encircling retinal tears) to three spot diameters (e.g. for treating conditions such as lattice degeneration). With even moderate divergence of the beam 22 exiting the optical fibers, the beam spot separation would be highly variable based upon the working distance WD.

Figure 12:
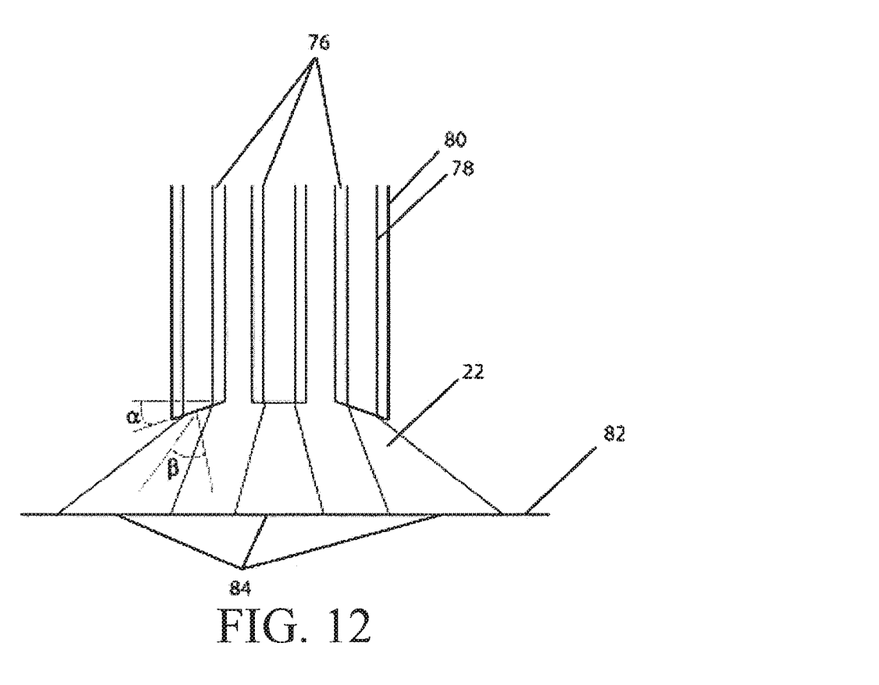
FIG. 12 is a side view illustrating the spots of light on the target tissue, and polishing angles of the fiber output ends that can extend variations of the working distance without causing the spots to overlap.

To provide more clinical utility by allowing for greater variation in working distance WD, the output ends 54 of the two outer optical fibers (but not the central fiber) can be polished at an angle to steer the beam 22 exiting the outer fibers 76 off-axis, as illustrated in FIG. 12. In this embodiment, the beam 22 is directed away from the center of the array by angle β according to the relation, $$\beta = \text{Sin}^{-1}\left(\left(\frac{n_{core}}{n_{env}}\right)\sin(\alpha)\right) \tag{2}$$

where $n_{core}$ and $n_{env}$ are the index of refraction of the fiber core 78 and the environment surrounding it (e.g. aqueous solution in which target tissue resides), respectively, and angle α is the polish angle of the fiber exit face (relative to the perpendicular of the longitudinal direction of the core 78). Having at least some of the exit faces of the output ends 54 not oriented parallel to a common plane allows for greater variation in working distance WD before the beam spots 84 overlap on tissue 82. In this configuration, the rotational alignment of the fibers 76 is important, since the fiber face angle α for the outer fibers 76 must be angled toward each other for the desired effect.

Figure 13:
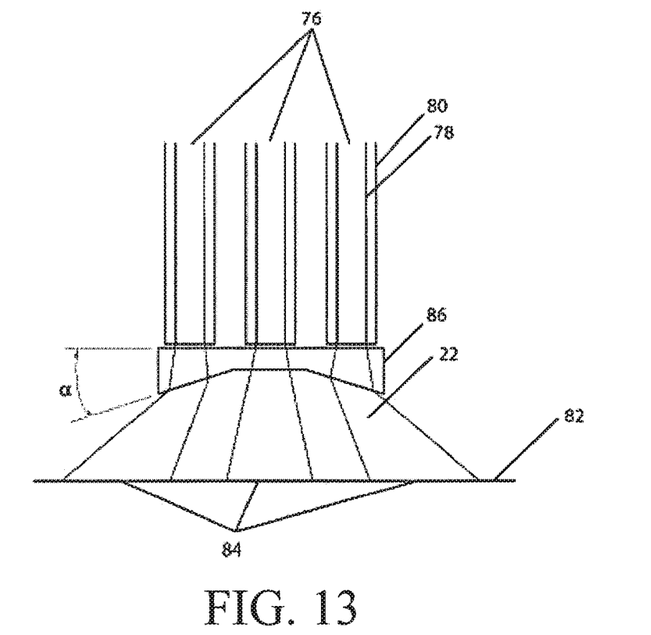
FIG. 13 is a side view illustrating the spots of light on the target tissue, and an optical element for steering the beams in a manner that can extend variations of the working distance without causing the spots to overlap.

FIG. 13 illustrates an embodiment which accomplishes the same effect as the angle polish of the embodiment described in FIG. 12, but without any rotational alignment constraints of the fibers. This embodiment uses a separate optical element for deflecting the beam, such as a zone plate 86. Zone plate 86 is an optical element that includes separate portions having different exit face angles α (relative to the perpendicular of the longitudinal direction of the core 78) for deflecting some of the beams more than others. Furthermore, zone plate 86 can be made with a rectangular perimeter, making it easy to align the zone plate 86 to an array of fibers. Zone plate 86 may also be provided with an anti-reflection coating to maintain system throughput efficiency. Such a tilted beam configuration naturally causes the beams to impinge on tissue obliquely. Thus, the spot size on tissue is enlarged by an obliquity factor, $F_o$ where $$F_o = \frac{1}{\sin(\beta - \alpha)}. \quad (3)$$

Figure 14:
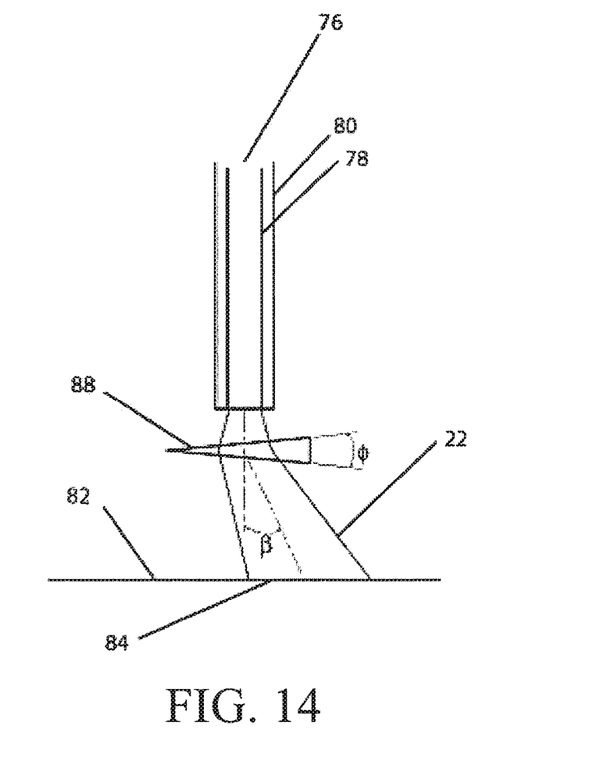
FIGS. 14-15 are side views illustrating a spot of light on the target tissue, and one or more wedge shaped optical elements for steering the beam in a manner that can extend variations of the working distance without causing the spots to overlap.
Figure 15:
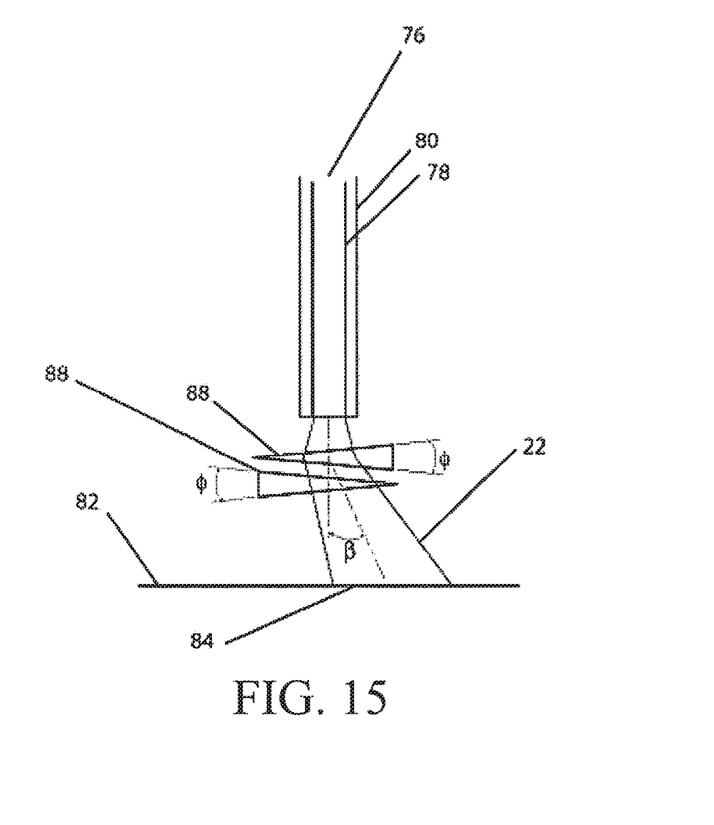

FIG. 14 illustrates the use of a wedge shaped optical element 88 to deflect the beam 22 by an amount β, where β=φ(n−1), and where φ is the wedge angle (i.e. angular difference between the entrance and exit faces of the wedge 88). A plurality of wedge shaped optical elements 88 may be used instead of the zone plate 86 to achieve the beam deflections of FIG. 13. In fact, even a plurality of wedge shaped optical elements 88 (with the same or different wedge angle φ) can be used serially to deflect the beam 22, as illustrated in FIG. 15. An alternative to the use of wedges to deviate the beam is the use of a de-centered lens. If decentered by an amount δ, a lens of focal length FL will create an angular deviation D, where $$D = \frac{\delta}{FL}. \quad (4)$$

Figure 16:
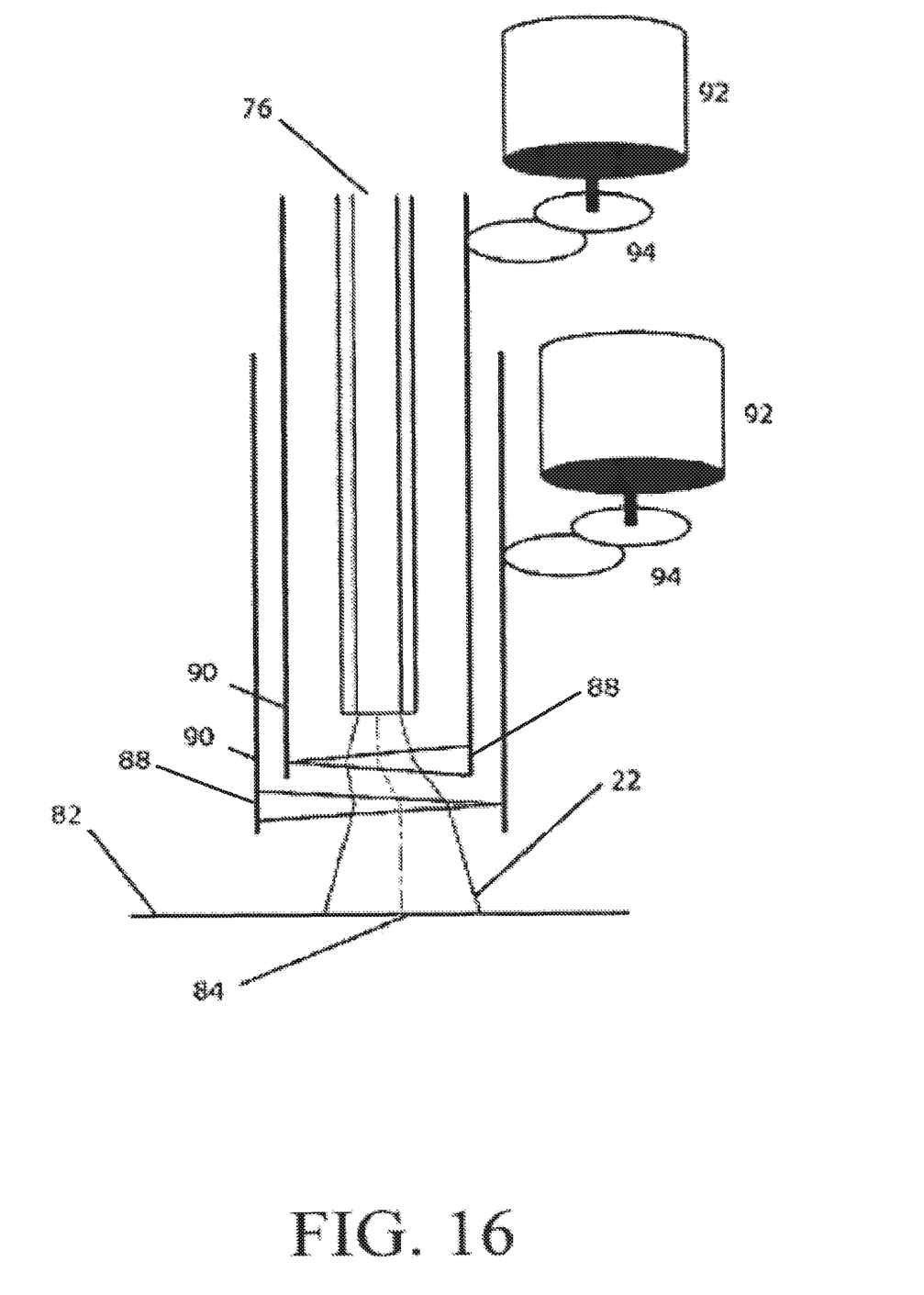
FIG. 16 is a side view illustrating a spot of light on the target tissue, and rotating wedge shaped optical elements for steering the beam in a manner that scans the beam in a circle pattern.

While static optical elements such as wedges, gratings, de-centered lenses, etc. achieve the goal of greater variation in working distance WD via beam deflection, the optical elements used to deflect the beam 22 exiting the probe tip 64 can be rotated to allow a circular pattern to be scanned on the target tissue. The beam 22 may be pulsed or cw, to deliver circular patterns of spots. Light may instead be delivered in a continuous manner to create contiguous circle patterns. FIG. 16 illustrates two wedges 88 that are rotated separately to provide true random access scanning in two dimensions. The two wedges 88 are mounted to separate sleeves 90, which are separately rotated by motors 92 via couplings 94.

Figure 17:
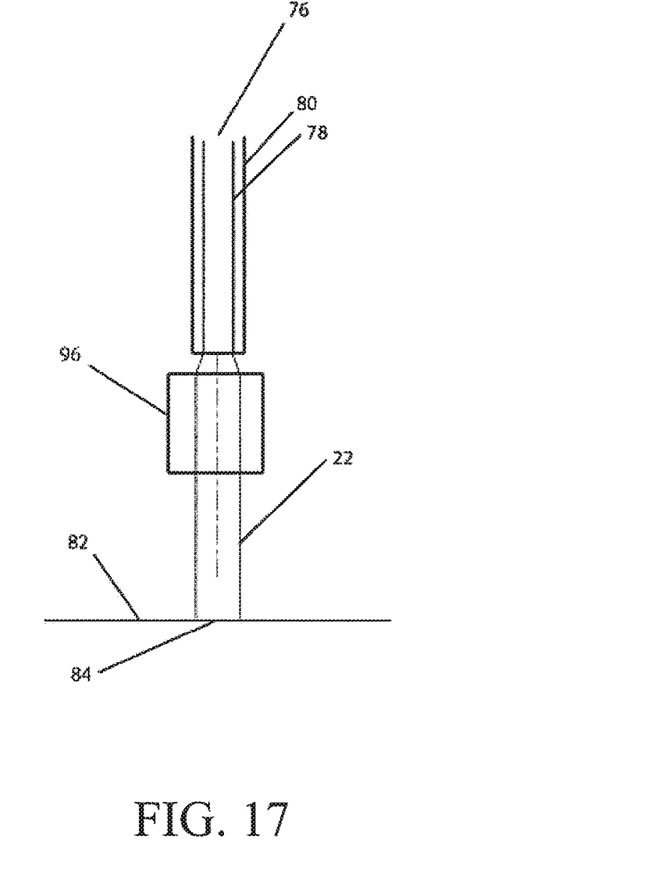
FIG. 17 is a side view illustrating a spot of light on the target tissue, and a focusing optical element for steering the beams in a manner that can extend variations of the working distance without causing the spots to overlap.

FIG. 17 illustrates another technique for providing a greater variation in working distance WD, which includes the use of a focusing optical element 96 to reduce or even eliminate the divergence of beam 22 exiting the optical fiber 76, which can be used alone or in conjunction with the embodiments described above. Examples of focusing optical element 96 include a high NA lens such as a ball, drum, or GRIN, which is placed after the fiber output face. It should be noted that the beam 22 will obey the rule that, at any surface in an optical system:

$$Dbeam*Sin(A)*n=L \quad (5)$$

where Dbeam is the diameter of the beam, n is the index of refraction of the environment, A is the divergence angle of beam, and L is a constant (i.e. the so called Lagrange invariant, an optical manifestation of the Second Law of Thermodynamics). This means that the beam can be allowed to expand to, say 3×, its diameter, which can reduce the beam spread to achieve a 3× longer working distance on the probe before the beams overlap. Specifically, a 100 μm core diameter, 0.12 NA fiber can produce a beam that may be allowed to propagate a distance of 1 mm in air to create a 300 μm beam. Focusing optical element 96 can be used to reduce the NA from 0.12, and yield a divergence angle A=40 mrad. This beam can then propagate 3.75 mm before doubling in size. Furthermore, in the case where focusing optical element 96 is a GRIN lens, the faces of such a lens may be angled to deviate the beam in the manner described above.

It is to be understood that the present invention is not limited to the embodiment(s) described above and illustrated herein, but encompasses any and all variations falling within the scope of the appended claims. For example, materials, processes and numerical examples described above are exemplary only, and should not be deemed to limit the claims. Any aspect of the present invention described herein may be combined with the other aspects described herein, to create a very flexible, robust, and clinically useful endoprobe. Any mirror can be replaced by any conventional optical element that reflects or refracts light (e.g. a prism). Deflection device 34 could translate mirror 32 instead of rotate it, where the change in beam deflection to different fibers is achieved via a curved reflective surface of mirror 32. Alternately, deflection device 34 could be configured to rotate or translate lens 36, or another optical element such as a grating or prism, to achieve the beam deflection change between the fibers. In fact, even an acousto-optical element can be used to deflect beam 22 into the selected fiber input ends. While the probe 14 sequentially projects spaced apart spots of the light beam 22 in the working distance, beyond the working distance the spots may no longer be spaced apart given the divergence of the light. However, even if the physician chooses to work outside the working distance with overlapping spots, or that the physician otherwise intentionally works at a distance where the spots overlap, that does not preclude a finding the spaced apart spots of the light beam 22 are still being projected from the probe and still exist at least at a point closer to the probe tip or at the probe tip given the physical spacing of the optical fibers at the probe tip. Lastly, while static and movable optical elements are described and illustrated for deflecting the beam exiting probe tip 64 containing fiber bundle 12, such optical elements could be used with a probe tip containing a single optical fiber.

What is claimed is:

1. A photomedical system for treating target tissue, comprising:
    a light source configured to generate a beam of light;
    an optical fiber having an input end configured to receive the beam of light and an output end configured to project the beam of the light;
    a probe having a tip configured to be inserted into an eye, wherein the output end of the optical fiber terminates at the probe tip;
    at least one optical element disposed adjacent the output end, the at least one optical element is configured to deflect the projected beam of light onto target tissue of the eye; and
    a device for moving the at least one optical element to change a direction of the deflection of the projected beam of light.

2. The photomedical system of claim 1, wherein the at least one optical element is an optical wedge having entrance and exit faces that are not parallel to each other.

3. The photomedical system of claim 1, wherein the at least one optical element is a plurality of optical wedges each having entrance and exit faces that are not parallel to each other.

4. The photomedical system of claim 1, further comprising:
    a second optical element disposed adjacent the output end for focusing the projected beam of light.

5. The photomedical system of claim 4, wherein the second optical element reduces a divergence of the projected beam of light.

6. The photomedical system of claim 1, further comprising:
    a mirror configured to deflect the light beam into the input end of the optical fiber.

7. The photomedical system of claim 1, further comprising:
a fiber optic switch configured to deflect the light beam into the input end of the optical fiber.

8. The photomedical system of claim 1, further comprising:
a conduit that extends along the optical fiber.

9. The photomedical system of claim 8, wherein the conduit is hollow for conveying a liquid.

10. The photomedical system of claim 8, wherein the conduit is a second optical fiber for conveying illumination light to or visualization light from the target tissue.

11. The photomedical system of claim 1, further comprising:
a second light source for generating a second beam of light, and
a mirror configured to deflect the second light beam into the input end of the optical fiber to project from the output end of the optical fiber at the probe tip.

12. The photomedical system of claim 1, wherein the at least one optical element is a zone plate having at least two portions with exit face angles that vary from each other for deflecting the projected beam of light in at least two directions not parallel to each other.

13. The photomedical system of claim 1, wherein the device for moving comprises:
one or more motors configured to rotate the at least one optical element.

14. The photomedical system of claim 1, wherein the device for moving comprises:
one or more couplings connected to one or more motors, wherein the coupling are configured to rotate the at least one optical element.

15. A method for treating target tissue, comprising:
generating a beam of light;
focusing the beam of light into an input end of an optical fiber;
projecting the beam of light out of an output end of the optical fiber, wherein the output end of the optical fiber terminates at a tip of a probe configured to be inserted into an eye;
deflecting the projected beam of light onto target tissue of the eye using an optical element disposed adjacent the output end of the optical fiber; and
moving the optical element to change a direction of the deflection of the projected beam of light.

16. The method of claim 15, further comprising:
focusing the projected beam of light using a second optical element disposed adjacent the output end of the optical fiber.

17. A photomedical system for treating target tissue, comprising:
a light source configured to generate a beam of light;
an optical fiber having an input end configured to receive the beam of light and an output end configured to project the beam of the light;
a probe having a tip configured to be inserted into an eye, wherein the output end of the optical fiber terminates at the probe tip;
at least one optical element disposed adjacent the output end, the at least one optical element is configured to deflect the projected beam of tight onto target tissue of the eye; and
a motor configured to rotate the at least one optical element to change a direction of the deflection of the projected beam of light.

18. The photomedical system of claim 17, wherein the at least one optical element is an optical wedge having entrance and exit faces that are not parallel to each other.

19. The photomedical system of claim 17, wherein the at least one optical element is a plurality of optical wedges each having entrance and exit faces that are not parallel to each other.

20. The photomedical system of claim 17, further comprising:
a second optical element disposed adjacent the output end configured to focus the projected beam of light.

21. The photomedical system of claim 20, wherein the second optical element reduces a divergence of the projected beam of light.

22. The photomedical system of claim 17, further comprising:
a conduit that extends along the optical fiber.

23. The photomedical system of claim 22, wherein the conduit is hollow for conveying a liquid.

24. The photomedical system of claim 22, wherein the conduit is a second optical fiber for conveying illumination light to or visualization light from the target tissue.

25. The photomedical system of claim 17, further comprising:
a second light source for generating a second beam of light, and
a mirror configured to deflect the second tight beam into the input end of the optical fiber to project from the output end of the optical fiber at the probe tip.

26. The photomedical system of claim 17, wherein the at least one optical element is a zone plate having at least two portions with exit face angles that vary from each other for deflecting the projected beam of light in at least two directions not parallel to each other.

27. The photomedical system of claim 17, further comprising:
a mirror configured to deflect the light beam into the input end of the optical fiber.

28. The photomedical system of claim 17, further comprising:
a fiber optic switch configured to deflect the light beam into the input end of the optical fiber.

29. A photomedical system for treating target tissue, comprising:
a light source configured to generate a beam of light;
an optical fiber having an input end configured to receive the beam of light and an output end configured to project the beam of the light;
a probe having a tip configured to be inserted into an eye, wherein the output end of the optical fiber terminates at the probe tip;
at least one optical element disposed adjacent the output end, the at least one optical element is configured to deflect the projected beam of light onto target tissue of the eye; and
one or more couplings connected to one or more motors configured to move the at least one optical element to change a direction of the deflection of the projected beam of light.

30. The photomedical system of claim 29, wherein the at least one optical element is an optical wedge having entrance and exit faces that are not parallel to each other.

31. The photomedical system of claim 29, wherein the at least one optical element is a plurality of optical wedges each having entrance and exit faces that are not parallel to each other.

32. The photomedical system of claim 29, further comprising:
a second optical element disposed adjacent the output end for focusing the projected beam of light.

33. The photomedical system of claim 32, wherein the second optical educes a divergence of the projected beam of light.

34. The photomedical system of claim 29, further comprising:
a conduit that extends along the optical fiber.

35. The photomedical system of claim 34, wherein the conduit is hollow for conveying a liquid.

36. The photomedical system of claim 34, wherein the conduit is a second optical fiber for conveying illumination light to or visualization light from the target tissue.

37. The photomedical system of claim 29, further comprising:
a second light source for generating a second beam of light, and
a mirror configured to deflect the second light beam into the input end of the optical fiber to project from the output end of the optical fiber at the probe tip.

38. The photomedical system of claim 29, wherein the at least one optical element is a zone plate having at least two portions with exit face angles that vary from each other for deflecting the projected beam of light in at least two directions not parallel to each other.

39. The photomedical system of claim 29, further comprising:
a mirror configured to deflect the light beam into the input end of the optical fiber.

40. The photomedical system of claim 29, further comprising:
a fiber optic switch configured to deflect the light beam into the input end of the optical fiber.

* * * * *